United States Patent
Kiernan, Jr.

(10) Patent No.: US 8,252,299 B1
(45) Date of Patent: Aug. 28, 2012

(54) MINIMUM RISK LIQUID NATURAL INSECT REPELLENT FOR GNATS

(75) Inventor: James Joseph Kiernan, Jr., Salt Springs, FL (US)

(73) Assignee: James Joseph Kiernan, Jr., Salt Springs, FL (US)

( * ) Notice: Subject to any disclaimer, the term of this patent is extended or adjusted under 35 U.S.C. 154(b) by 243 days.

(21) Appl. No.: 12/802,593

(22) Filed: Jun. 10, 2010

(51) Int. Cl.
*A01N 25/00* (2006.01)

(52) U.S. Cl. ........................................... 424/405

(58) Field of Classification Search .................. None
See application file for complete search history.

(56) References Cited

U.S. PATENT DOCUMENTS

| 6,472,351 | B1 * | 10/2002 | Ryan et al. | 504/320 |
| 2004/0242703 | A1 * | 12/2004 | Roe | 514/693 |
| 2007/0098750 | A1 * | 5/2007 | Bessette | 424/405 |

OTHER PUBLICATIONS

Toxnet, Citronellal (2002), pp. 1-13.*
Bayou, BayouSome.com, Inc., PET Bottle (Jun. 22, 2008) pp. 1-11.*
Kesoon, Paraffin Oil (Sep. 14, 2004) pp. 1-6.*

* cited by examiner

*Primary Examiner* — Scott Long
*Assistant Examiner* — Lyndsey Beckhardt

(57) ABSTRACT

An minimum risk liquid natural insect repellent which comprises citronella java type oil as the active repellency for the use against biting gnats and the inactive ingredient is low viscosity white mineral oil petroleum type and is a secondary means of protection, and isopropyl myristate as the emulsifier. In a process which consists of a free gas injection vacuum batch mixture procedure.

11 Claims, No Drawings

MINIMUM RISK LIQUID NATURAL INSECT REPELLENT FOR GNATS

FIELD OF THE INVENTION

This invention relates to a composition of matter and process for a minimum risk liquid natural insect repellent that provides effective protection for humans and pets against biting gnats with out the use of harmful chemicals.

BACKGROUND OF THE INVENTION

Overall objectives were to develop a minimum risk natural insect repellent being free of DEET and any harmful chemicals that would be safe for use on human adults, children and pets. Target biting gnats. Have a pleasant aroma. Have an attractive look for use in a clear spray bottle and be safe for the environment.

Citronellal and citronella oil has been used for over 50 years as an insect repellent, and it is found in many insect repellent products. The two varieties of citronella oil used commercially are Ceylon type derived from C. nardus and Java type derived from C. winterianus. These products vary in efficacy, repel various insects some of which are public health pest, such as gnats, mosquitoes, biting flies and fleas. When used according to the label, citronella products are not expected to cause harm to humans, pets or the environment. Citronella is considered so unlikely to cause harmful effects that some citronella products are exempt from the usual regulation. However, registration is required for those products that do not meet the criteria for exemption (for instance, they contain other ingredients that the Environmental Protection Agency (EPA) has not classified as minimal risk).

This invention meets the qualifications as an (exempted) minimum risk pesticide under 40 CFR 152.25 (g) and FIFRA 25 (b) of the EPA regulations. Because of its safe nature, this said invention is also allowed to be mailed thru the United States Postal Service. And with today's green mentality and concern for the environment it is a very important part of this invention.

Considerable time was spent perfecting and testing the composition and mixture percentage and types of ingredients to determine the effective ratios of the ingredients to repel the gnats belonging to the ceratopogonidae family and to perfect the free oxygen gas vacuum transparency conversion process.

Blending of the three above mentioned ingredients is phenomenal once this mixing and or the bonding process is complete. No mater how long or at what position the finished product sits in the bottle there is no separation of ingredients at all, this gives equal amounts of protection in every spray from the bottle for maximum insect repellent protection.

This process also helps determine the clear clarity characteristics of the invention as claimed, important for consumer attractiveness.

SUMMARY OF THE INVENTION

The invention as claimed provides a composition for the repelling of a target species scientific name culicoides furens. Common names, sand gnat, biting midge, punky, sand flies and noseeums. They belong to the Ceratopogonidae family and the Diptera order. Gnats don't just puncture your skin like mosquitoes do. Instead they rip it open using sharp cutting teeth located on the mandible. After inserting two sharp sword like blades into the skin like anchors, the biting gnat uses cutting teeth to rip up the skin and get the blood flowing, then squirts a chemical into the open wound to inhibit blood clotting. The tiny pool of blood that forms is then sucked up through a straw like structure called the proboscis. Some victims, human or animal have allergic reactions to the chemical and must endure itchy red spots or even swollen welts. Breeding areas can be varied but include salt marsh habitats, mud, sand margins of rivers, lakes, ponds etc. they can also be found in decaying leaf mould and tree hide. Using traditional insecticides and repellents kill the gnats and gnat larvae which are an important food source for other species found in the salt marshes and estuaries. This said invention repels the gnat but does not kill them or harm the user or environment The invention as claimed composition comprises the active ingredient Java type citronellal oil. Cas. Reg. no. 106-23-0 obtained from cymbopogon winterianus jowitt, consists of citronellal (32-45%), geranial (11-13%). Geranyl accetate (3-8%), limonene (1-4%). The higher proportion of citronellal make it a better source for insect repellents. Ceylon type obtained from Cymbopogon nardus Rendle consists of geranial (18 to 20%), limeene (9 to 11%), methylisoeugenol (7 to 11%), citronellol (6 to 8%), and citronellal (5 to 15). It was found that 14 percent by volume of citronellal was the best amount for repelling the biting gnat, the ratio up to 20 percent is for longer repellency time. Citronella oil is a renowned plant based insect repellent, and has been registered for this use in the United States since 1948. The United States Environmental Protection Agency (EPA) considers oil of citronella as a biopesticide with a non-toxic mode of action. The amount of citronellal used in the mixture was determined by testing on willing male and female humans. Dogs, cats and horse's to obtain the optimum repelling effect against the target species.

The testing area of the invention was from the Okefenokee swamp area to the southeast area of Georgia, northeastern and central Florida. Testing showed conclusive evidence and data confirmed the effectiveness of the composition or formula to effectively repel targeted species.

DRAWINGS

"NOT APPLICABLE"

Testing on willing humans was conducted with two personnel at a time in gnat biting invested areas of Camden county Ga. Who were stationary post civilian guards for 8 hours at a time. Individuals were asked to use said composition and fill out questionnaire, six different posts for 2 weeks for a total of 1344 man hours of testing. Among other Statistics effectiveness in repelling gnats was the primary test. Questionnaires were Annualized and guards were asked about the effectiveness of the composition, results were said composition repels biting gnats for various durations depending on temperature, weather, the individual and was overall very effective in repelling biting gnats.

Two 3 ft.×3 ft. areas were taped off, in a known biting gnat area and was swept with a net to capture and count gnats per area but not the taped area, approximately 75 gnats were found per 3 ft.×3 ft. area. One area was treated one area was not and left for 1 hour. Area that was treated had zero biting gnats, area not treated had approx. 62 biting gnats.

A group of $6^{th}$ graders under the supervision of there teacher on a zoo trip were given samples of said composition. The children had no ill effects and complete relief from the biting gnats while the others around them were annoyed and harassed by the biting gnats in the zoo area.

Testing was conducted with 50 individuals camping, hiking and fishing in the Ockeefenokee swamp area and KOA camp ground in southern Ga. Testing was also conducted in the Fernadina area of Florida, all biting gnat habitat areas, individuals were given samples with mail in questionnaires or on the spot interviews, test results showed conclusively that said composition repelled the biting gnats.

Cars parked with their windows down, one vehicle was treated with said composition and the other was not, and let sit for 1 hour in biting gnat area approx. 10 ft. apart. Car treated: number of gnats counted after 1 hour 15 gnats. Car untreated: number of gnats counted after 1 hour 197 gnats.

Testing was conducted in biting gnat invested areas using dogs over a period of 3 days. Four dogs were sprayed with the said composition and allowed to play for 1 hour and checked for bites, None of the dogs exhibited the red marks or welts associated with the bites of the gnats. The next day the dogs were not treated and allowed to play for 1 hour, all the dogs suffered from gnat bites on there bellies and were constantly harassed by the gnats while playing. The third day 2 dogs were treated and 2 dogs were not, again the dogs that were not treated suffered from gnat bites while the treated dogs were bite free.

Testing was also conducted on horse's in the Ocala, Fla. area by the owner of the animals and was found to be very effective for relief of the horse's from biting gnats.

DETAILED DESCRIPTION OF THE INVENTION

The active ingredient for repellency is citronellal oil java type cas registration number 106-23-0 was found to be the best type of natural repellent for the targeted species, the biting gnat.

The inactive or inert ingredients used are white mineral oil (petroleum) low viscosity, cas reg. no. 8042-47-5. The white mineral oil is not used as an emollient, but to serve as a secondary barrier against any gnats that penetrate the repellent, the gnats are very small, get stuck and cannot bite. And isopropyl myristate cas reg. no. 110-27-0. Isopropyl myristate serves as an emulsifier, perfect for this composition because it has an oil loving hydrophobic tail. The mixture proportions were determined under trial and era testing. Batch mixing is a dual process of Free oxygen gas injection and pressure vacuum and was the best methods of said invention to meet all requirements. These methods obtained the desired clear appearance with no seperation of ingredients.

It was found that certain types of bottle material were not suitable and would deform or contract from a combination of the ingredients used and summer heat, the best bottle found to fix these problems was a Cosmo PET clear bottle with atomizer.

These three above mentioned ingredients are considered minimum risk active and inactive ingredients for use in pesticides by the EPA and the active ingredient can be found in the list 40 Code of Federal Regulations (CFR) 152.25 (g). The inert ingredients can be found on the list 4A (40 CFR 180.950).

The invention as claimed composition is bonded/cured by the process of being under a vacuum in a kettle that was modified. A vacuum removes the top air from the kettle and provides a low oxygen atmosphere and keeps the ingredients under pressure during curing and or bonding time. Vacuum is accomplished using a non collapsible hose attached to a fitting on the kettle inline with a pressure gauge using a small vacuum pump. With pressure at 33 psi to 37 psi (35 psi optimum, plus or minus 2 psi).

Free oxygen gas injection is used to saturate the mixture during batch mixing to start the process of bonding, and was found to be the best method for this process.

It is the object of this invention to provide protection from biting gnats. It is another object of the present invention to use minimum risk ingredients. It is still another object of this invention for it to be safe for humans and pets. It is still another object of said invention to be safe for the environment. Therefore there has now been found a minimum risk gnat repellent with a high percentage of citronellal oil from about 14 to 20 percent by volume that does not separate under the influence of the other ingredients and further has no discoloration.

Other publications.
United States Environmental Protection Agency R. E. D. FACTS.
Minimum Risk Pesticides under FIFRA Section 25 (b) US EPA.
Citronella oil (021901) Fact Sheet US EPA.
Citronellal, The Merck Index, 12$^{th}$ Edition.
Citronellal—Wikipedia The composition and process is prepared by batch mixing the ingredients in the following order: isopropyl myristate by volume ratio of 14 percent to 20 percent (+ or −1%) into a vacuum kettle. Free oxygen gas is injected (preferred method air regulated moisture filtered pump 3 psi to 7 psi). Low viscosity white light mineral oil (petroleum) by ratio of volume 65 percent to 72 percent (+ or −2%) blend for five minutes by stirring with a (preferred method a cedar wooden paddle), with continued free oxygen gas injected. Add citronellal oil by ratio of volume 14 percent to 20 percent (+ or −1%) stirring for six minutes, with continued free oxygen gas injection. Bonding and curing process is accomplished under pressure at a vacuum of 33 psi to 37 psi. bonding time depends on purity and concentration by volume of the citronellal oil and is completed in 8 to 12 hours.

Ingredients of composition of matter.
Active Ingredient:
(1). Citronellal Java type oil. Cas reg. no. 106-23-0. Chemical formula C10H18O.
Inactive Ingredients:
(2). White mineral oil (petroleum) low viscosity. Cas. Reg. no. 8042-47-5. Chemical formula (CH2)n 20=<n=<40.
(3). Isopropyl myristate. Cas. Reg. no. 110-27-0. Chemical formula

CH3(CH2)12C00CH(CH3)2.

>The final mixture is placed in 2 ounce clear bottles with spray mister and is percentage (%) by volume, the following.
>The best bottle to meet all requirements of said invention was a cosmo PET with atomizer.

| | | |
|---|---|---|
| (1). Citronellal oil | 1:5:1 or 1.5:4:1.5 | percentage by volume. |
| (2). White mineral oil | 5:1:1 or 4:1.5:1.5 | percentage by volume. |
| (3). Isoproply myristate | 1:1:5 or 1.5:4:1.5 | percentage by volume. |

What is claimed is:
1. A composition formula as a minimum risk liquid natural insect repellent for humans and pets to repel a target pest, that does not injure the environment, consisting of: (A) 14.4 percent to 20 percent by volume citronellal java type oil cas registration number 106-23-0, (B) 65 percent to 72 percent by volume, white mineral oil (petroleum) low viscosity cas registration number 8042-47-5, (C) 14 percent to 20 percent by volume isopropyl myristrate cas registration number 110-27-0.

2. The composition of claim 1 is a minimum risk natural insect repellent.

3. The composition of claim 1 is safe for the environment.

4. The composition of claim 1 wherein the target pest is a biting gnat.

5. The composition of claim 1 is safe for use around humans and pets.

6. A method of making a composition formula as a minim risk liquid natural insect repellent for humans and pets to repel target pests consisting of batch mixing the ingredients in the following order:
  a) adding isopropyl myristrate by volume ratio of 14 percent to 20 percent (+ or −1%) into a vacuum kettle,
  b) injecting free oxygen gas,
  c) adding low viscosity white mineral oil (petroleum) by ratio of volume 65 percent to 72 percent (+ or −2%),
  d) blending for five minutes by stirring with continued free oxygen gas injection,
  e) adding citronellal oil by ratio of volume 14 percent to 20 percent (+ or −1%),
  f) stirring for six minutes with continued free oxygen gas injection,
  g) applying pressure as a vacuum for 8 to 12 hours.

7. The method of claim 6, wherein the free oxygen gas injection is at three to seven psi, and wherein the vacuum is at thirty three to thirty seven psi.

8. The composition of claim 1 is a clear in clarity liquid.

9. The composition of claim 1 exhibits no separation of ingredients.

10. A kit comprising the composition of claim 1, wherein the composition is packaged in a PET bottle with atomizer.

11. The kit of claim 10, wherein the PET bottle is clear.

\* \* \* \* \*